(12) United States Patent
Anukhin et al.

(10) Patent No.: US 7,112,055 B1
(45) Date of Patent: Sep. 26, 2006

(54) NITINOL FRAME HEATING AND SETTING MANDREL

(75) Inventors: Boris Anukhin, San Jose, CA (US); Masoud Molaei, Fremont, CA (US); David T. Pollock, Redwood City, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 377 days.

(21) Appl. No.: 10/188,812

(22) Filed: Jul. 2, 2002

(51) Int. Cl.
*B29C 53/42* (2006.01)

(52) U.S. Cl. ............... 425/365; 425/468; 425/DIG. 14; 249/100; 249/175; 72/342.1

(58) Field of Classification Search ................. 425/365, 425/DIG. 10, 467, 468; 249/100, 175, 176; 72/342.1
See application file for complete search history.

(56) References Cited

U.S. PATENT DOCUMENTS

| 696,289 A | 3/1902 | Williams |
|---|---|---|
| 2,964,088 A | 12/1960 | Erath |
| 4,455,854 A | 6/1984 | Ermolovich |
| 4,468,224 A | 8/1984 | Enzmann et al. |
| 4,576,142 A | 3/1986 | Schiff |
| 4,644,936 A | 2/1987 | Schiff |
| 4,681,092 A | 7/1987 | Cho et al. |
| 4,697,573 A | 10/1987 | Schiff |
| 4,901,707 A | 2/1990 | Schiff |
| 4,907,336 A | 3/1990 | Gianturco |
| 5,132,066 A | 7/1992 | Charlesworth et al. |
| 5,133,732 A | 7/1992 | Wiktor |
| 5,183,085 A | 2/1993 | Timmermans |
| 5,189,786 A | 3/1993 | Ishikawa et al. |
| 5,437,083 A | 8/1995 | Williams et al. |
| 5,546,646 A | 8/1996 | Williams et al. |
| 5,626,604 A | 5/1997 | Cottone, Jr. |
| 5,630,830 A | 5/1997 | Verbeek |
| 5,653,691 A | 8/1997 | Rupp et al. |
| 5,672,169 A | 9/1997 | Verbeek |
| 5,693,066 A | 12/1997 | Rupp et al. |
| 5,725,519 A | 3/1998 | Penner et al. |
| 5,738,674 A | 4/1998 | Williams et al. |
| 5,746,764 A | 5/1998 | Green et al. |
| 5,746,765 A | 5/1998 | Kleshinski et al. |
| 5,759,474 A | 6/1998 | Rupp et al. |

(Continued)

FOREIGN PATENT DOCUMENTS

DE 464004 8/1928

(Continued)

OTHER PUBLICATIONS

The eXTraordinary Stent, C.R. Bard Brochure, undated.

*Primary Examiner*—Tim Heitbrink
*Assistant Examiner*—Thu Khanh T. Nguyen
(74) *Attorney, Agent, or Firm*—Fulwider Patton LLP

(57) ABSTRACT

An apparatus for heating and setting elements of a stent. The apparatus is a mandrel having a central core cylinder with an outer surface including a plurality of raised forms and gaps in-between the raised forms. The mandrel also includes a first and second outer cylinder, each having a curved radial end with a cut-out design similar to the shape of the plurality of raised forms. Once a stent is placed on the central core cylinder, the first and second outer cylinders are positioned on the central core cylinder such that the curved radial ends of the first and second outer cylinders align with the plurality of raised forms, shaping the stent.

9 Claims, 5 Drawing Sheets

U.S. PATENT DOCUMENTS

| | | |
|---|---|---|
| 5,772,864 A | 6/1998 | Moller et al. |
| 5,782,855 A | 7/1998 | Lau et al. |
| 5,782,903 A | 7/1998 | Wiktor |
| 5,783,227 A | 7/1998 | Dunham |
| 5,785,715 A | 7/1998 | Schatz |
| 5,787,572 A | 8/1998 | Toms |
| 5,788,558 A | 8/1998 | Klein |
| 5,800,526 A | 9/1998 | Anderson et al. |
| 5,810,838 A | 9/1998 | Solar |
| 5,810,871 A | 9/1998 | Tuckey et al. |
| 5,810,873 A | 9/1998 | Morales |
| 5,836,952 A | 11/1998 | Davis et al. |
| 5,893,852 A | 4/1999 | Morales et al. |
| 5,893,867 A | 4/1999 | Bagaoisan et al. |
| 5,920,975 A | 7/1999 | Morales |
| 5,931,851 A | 8/1999 | Morales |
| 5,944,735 A | 8/1999 | Green et al. |
| 5,947,993 A | 9/1999 | Morales |
| 5,948,191 A | 9/1999 | Solovay |
| 5,951,569 A | 9/1999 | Tuckey et al. |
| 5,972,016 A | 10/1999 | Morales |
| 5,974,652 A | 11/1999 | Kimes et al. |
| 6,009,614 A | 1/2000 | Morales |
| 6,024,737 A | 2/2000 | Morales |
| 6,051,002 A | 4/2000 | Morales |
| 6,063,092 A | 5/2000 | Shin |
| 6,063,102 A | 5/2000 | Morales |
| 6,074,381 A | 6/2000 | Dinh et al. |
| 6,092,273 A | 7/2000 | Villareall |
| 6,125,523 A | 10/2000 | Brown et al. |
| 6,141,855 A | 11/2000 | Morales |
| 6,193,829 B1 * | 2/2001 | Acciai et al. ............... 156/180 |
| 6,203,732 B1 * | 3/2001 | Clubb et al. ................ 264/81 |
| 6,245,099 B1 * | 6/2001 | Edwin et al. ............. 623/1.13 |
| 6,245,100 B1 | 6/2001 | Davila et al. |
| 6,279,368 B1 * | 8/2001 | Escano et al. ............ 72/342.1 |

FOREIGN PATENT DOCUMENTS

| | | |
|---|---|---|
| EP | 0 630 623 | 12/1994 |
| EP | 0 826 346 | 3/1998 |
| EP | 0 873 731 | 10/1998 |
| EP | 0 938 877 | 9/1999 |
| GB | 159065 | 2/1921 |
| WO | WO 98/14120 | 4/1998 |
| WO | WO 98/19633 | 5/1998 |

* cited by examiner

NITINOL FRAME HEATING AND SETTING MANDREL

BACKGROUND OF THE INVENTION

This application relates to heating and setting mandrels for use in manufacturing and more particularly, a mandrel for heating and setting a stent having limb elements which provide for improved expansion characteristics.

The term stent generally refers to a prosthesis, which can be introduced into a corporeal lumen and expanded to support that lumen or attach a conduit to the inner surface of that lumen. Self-expanding stents are generally known in the art. During use, the self-expanding stent is compressed into a reduced size having an outer diameter substantially smaller than the stent in its expanded shape. The stent is held in its compressed state during its passage through the patient's vascular system until reaching the target treatment site, whereupon the compressed self-expanding stent may be deployed. While in its compressed state, stress is stored in the bends of the stent limbs. During deployment, the stresses in the stent limbs cause the stent to expand radially from its initially compressed state. Once in place, the radial extremities of the stent bear against the inside walls of the passageway, thereby allowing normal blood flow.

The processes of manufacturing self-expanding stents are also known in the art insofar as heat treating a stent upon a mandrel for purposes of setting a particular stent shape. Additionally, shape memorization processes utilizing mandrels are stent specific as each stent-type embody different design requirements. Previous attempts at heat treating simply involve mounting a stent upon a mandrel and exposing it to heat with little attention being paid to the shape that is set, other than the diameter, during the heating process. Because these previous attempts fail to control the shape of the stent limbs created during the heating process, a less effective final stent is produced.

Most stents known in the art change diameter through the deformation of a small percentage of a length of the limbs defining the stent. Usually, this deformation occurs only at, or near, curved apices formed in stent limbs. The length of the limb that deforms and the magnitude of the deformation has a bearing on three important and interrelated characteristics of the stent: 1) the minimum diameter to which the stent can be compressed; 2) the radial stiffness or energy required to compress the stent; and 3) the maximum value of stress/strain experienced by the stent. Many other factors are also determinative of these characteristics including stent material, resting diameter, stent length, etc.; however, these other factors are assumed to be generally constant for a given stent design.

A stent having curved limb members can improve the above mentioned characteristics of the stent by spreading the deformation energy over a majority of the length of the stent limbs. This is in contrast to other stent designs that concentrate the deformation at or near the apices in the stent limb.

For example, to maximize radial stiffness and to minimize a compressed diameter of a stent, limb elements defining the stent each can embody two curves of constant radius and opposite direction which meet at an inflection point. When such a stent is compressed, the two curved sections assume a nearly straight profile, the advantage of which is that the entire length of the curved portions store deformation energy and function to urge the stent radially outward.

In the event a stent having curved limb members is to be manufactured, in order to set a desired expanded configuration the stent is expanded over a cylindrical mandrel and heated. However, merely expanding the stent over a mandrel without additional controls or constraints, rarely results in limb elements having the desired profile. To wit, the end of the limbs may be provided with a smaller than desired radius of curvature whereas the portion of the limbs near an inflection point may have a much larger than desired radius of curvature. This results in producing a stent that embodies limbs which do not store stress in an optimal manner. Therefore, an expansion mandrel for heating and setting a stent which facilitates the production of a desired stent profile as well as aids in evenly dispersing stresses along limb elements defining the stent during manufacturing was developed, and is described in U.S. Pat. No. 6,279,368 B1 to Escano et al. It would be beneficial to have an improved mandrel that makes the process of loading a stent onto a mandrel easier.

As is known, stents are currently expanded on a mandrel through multiple shape setting steps, and at some point before the last expansion, an additional ring is placed on the stent to help protrude hooks from the stent. This process is very slow and prone to damaging the stent. Therefore, an alternative process is needed to make the hook-setting step easier, faster, and less susceptible to damage.

The present invention satisfies these and other needs.

SUMMARY OF THE INVENTION

Briefly, and in general terms, the present invention provides an improved heating/setting mandrel which substantially reduces the difficulty in loading stents onto the mandrel. Moreover, the mandrel construction of the present invention is relatively inexpensive to manufacture, is trouble-free and reliable in use, and attains improved and constant results in the manufacture of stents having curved limb elements.

Furthermore, the present invention also provides an improved mandrel and method for setting hooks of a stent. The present invention makes the hook-setting step easier, faster, and the stent is less prone to damage.

In one aspect, the invention comprises a hollow central core cylinder made from a heat conducting material having an outer surface including a plurality of raised forms, gaps in-between the raised forms, and the central core cylinder has an outer surface diameter and a raised form diameter. The invention also includes a first and second outer cylinder, also made from a heat conducting material, and each having a curved radial end with a cut-out design similar to the shape of the plurality of raised forms. The first and second outer cylinders each have an inner diameter that is nearly equivalent to or slightly larger than the outer surface diameter of the central core cylinder, and the inner diameter is less than the raised form diameter. In operation, a stent is placed on the central core cylinder with the limb elements of the stent directed around the raised forms in the gaps in-between. Then, the first and second outer cylinders are slid onto the central core cylinder at opposite ends such that the curved radial ends of the first and second outer cylinders align with the plurality of raised forms and force the stent into the shape of the raised forms. The first and second outer cylinders may also include a plurality of hook extenders disposed at the curved radial ends which shape hooks of a stent. Once the stent and first and second outer cylinders are in place on the central core cylinder, heat is applied to the apparatus to shape set the stent.

In another aspect, the invention further includes a capture sleeve having a cylindrical shape with an inner diameter nearly equivalent to or slightly larger than the raised form diameter of the central core cylinder. The capture sleeve fits over the central core cylinder and the plurality of raised forms, leaving an insert space for the first and second outer cylinders to be inserted between the capture sleeve and the central core mandrel.

In yet another embodiment, the present invention includes a mandrel having an outer surface with a plurality of slots disposed thereon corresponding to the position of hooks on a stent. In conjunction with this mandrel, first and second stop rings may be used to engage opposite ends of the mandrel and to press against ends of the stent, holding the stent in place on the mandrel. A method of using this mandrel includes turning a stent inside-out, and positioning the stent on the mandrel such that the hooks are aligned with the plurality of slots. Once on the mandrel, the hooks are then pushed into the slots, and the apparatus and stent are heated to set the hooks.

Other features and advantages of the present invention will become apparent from the following detailed description, taken in conjunction with the accompanying drawings, which illustrate, by way of example, the principles of the invention.

DETAILED DESCRIPTION OF THE INVENTION

The present invention is directed to an improved mandrel for use in heating and setting a stent having curved limb elements which alleviates the stresses inflicted upon the limbs of the stent during the manufacturing. The mandrel shapes the limbs of the stent during the heating process by employing the use of raised forms and outer cylinders which hold in place the limb portions of the stent to thereby produce a stent with limb portions having constant radius of curvatures.

Figure 1:
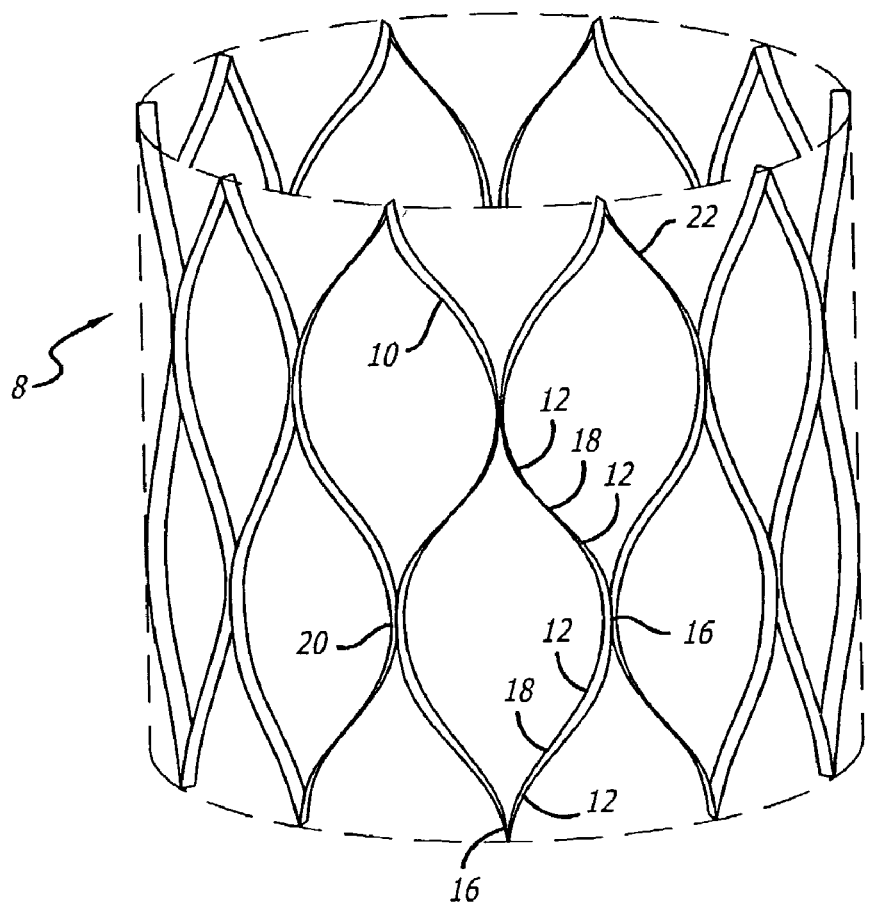
FIG. 1 is a perspective view with some elements in the background not shown for clarity, depicting a stent having curved limb elements to be manufactured with the present invention.
Figure 2:
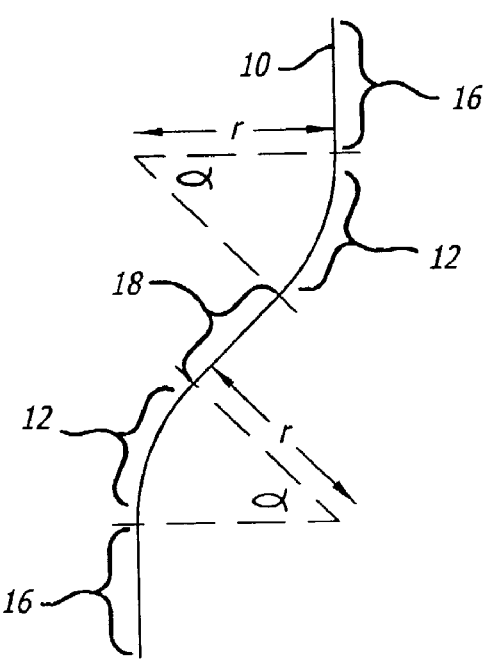
FIG. 2 is a side view, depicting a single curved limb element of the stent of FIG. 1.

Referring now to the drawings, in FIG. 1, there is shown an example of a stent 8 having curved limb elements to be manufactured with the present mandrel invention. Such a stent 8 may be cut from a tube or assembled from separate elements. FIG. 2 depicts a repeating element of each limb 10 of a stent cell, having two curved elements 12 of equal radius, equal length and opposite direction. The short straight segment element 16 at the ends of each limb 10 are parallel to one another. The mid-portion or the inflection point 18 lies between the two curved segment elements 12 of each stent limb 10.

Figure 3:
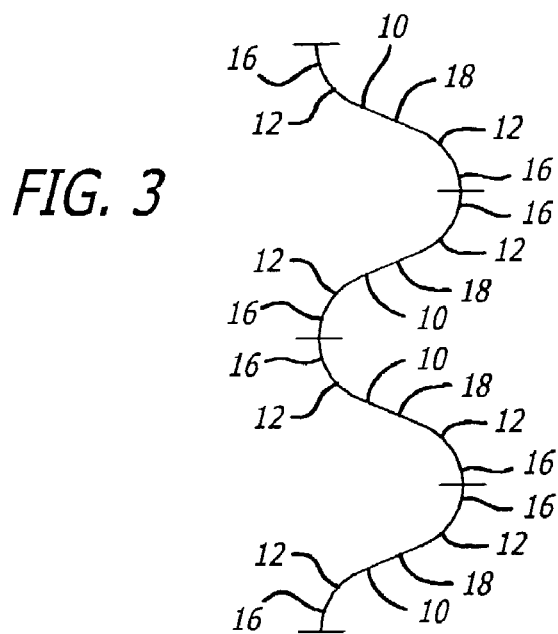
FIG. 3 is a side view, depicting a curved limb element of a stent to be used in the present invention.
Figure 4:
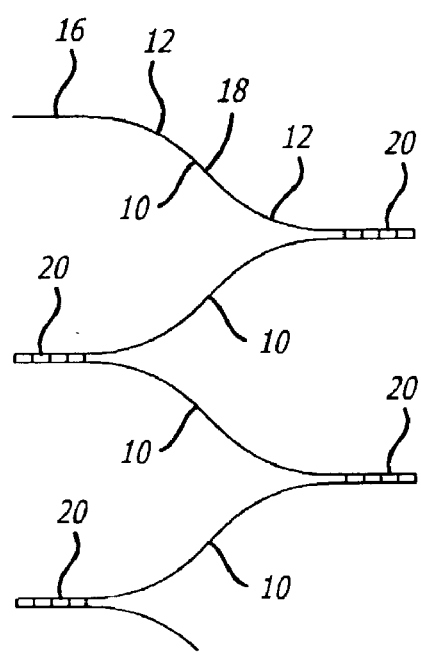
FIG. 4 is a side view, depicting typical joints between adjacent curved limb elements in a stent which is comprised of a multiplicity of such curved limb elements.

Referring to FIG. 3, depending on the overall length of the stent, the limb element 10 may bend back and forth in a sinusoid wave pattern down the length of the stent 8. Additionally, referring to FIG. 4, in the event the stent 8 is made from separate elements, the short straight segment elements 16 of adjacent limbs maybe joined, either by welding, soldering, riveting, or gluing to form joint 20. A multiplicity of identical limb elements can be joined in this way to form the cylindrical stent structure, as seen in FIG. 1.

Figure 5:
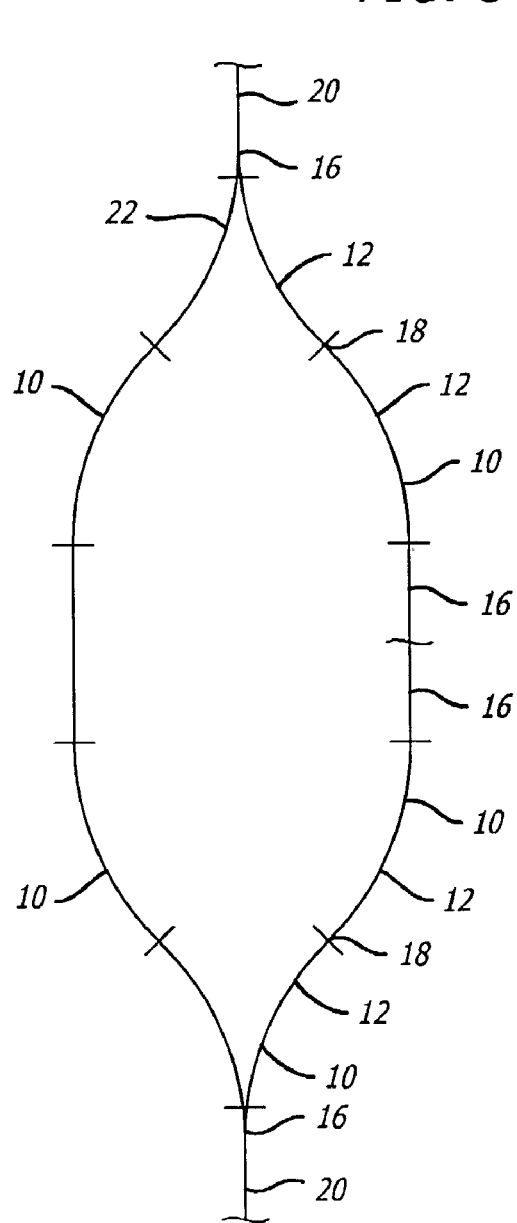
FIG. 5 is a side view, depicting an almond shaped stent cell of a stent to be used in the present invention.

Referring to FIG. 5, a stent cell 22 may have an almond-like shape and each cell may embody four limb elements 10. Each limb 10 essentially comprises a quarter of a full stent cell 22. As described above, one limb 10, making up a quarter of the stent cell 22, starts from the midpoint of the stent cell to the end of the stent cell. The limb elements 10 are comprised of two curve elements 12. These curve elements 12 are of equal radius, equal length and opposite direction. In a preferred stent embodiment, the limb 10 would be composed of two curves having constant radius r with an inflection point 18 in the middle where they reverse direction.

Under ideal conditions, it is preferred that the stress along the length of the limb 10 be as evenly distributed as possible so that there is minimal or no stress at the inflection point 18. Along the rest of limb 10, the stress level will be determined by the inverse of the radius r that the stent 8 limb has in its relaxed configuration. During introduction into vasculature, the stent 8 is compressed down into a catheter (not shown). In this compressed configuration, the curved limb elements 12 become generally straight. The change in radius r of curvature from the compressed state where the limbs 10 are straight to its profile in a relaxed state has a bearing on the amount of stress. The stress along the limb 10 and the amount of energy that can be stored in the stent 8 is determined by the change in the radius of curvature at any point along the limb 10.

Figure 6:
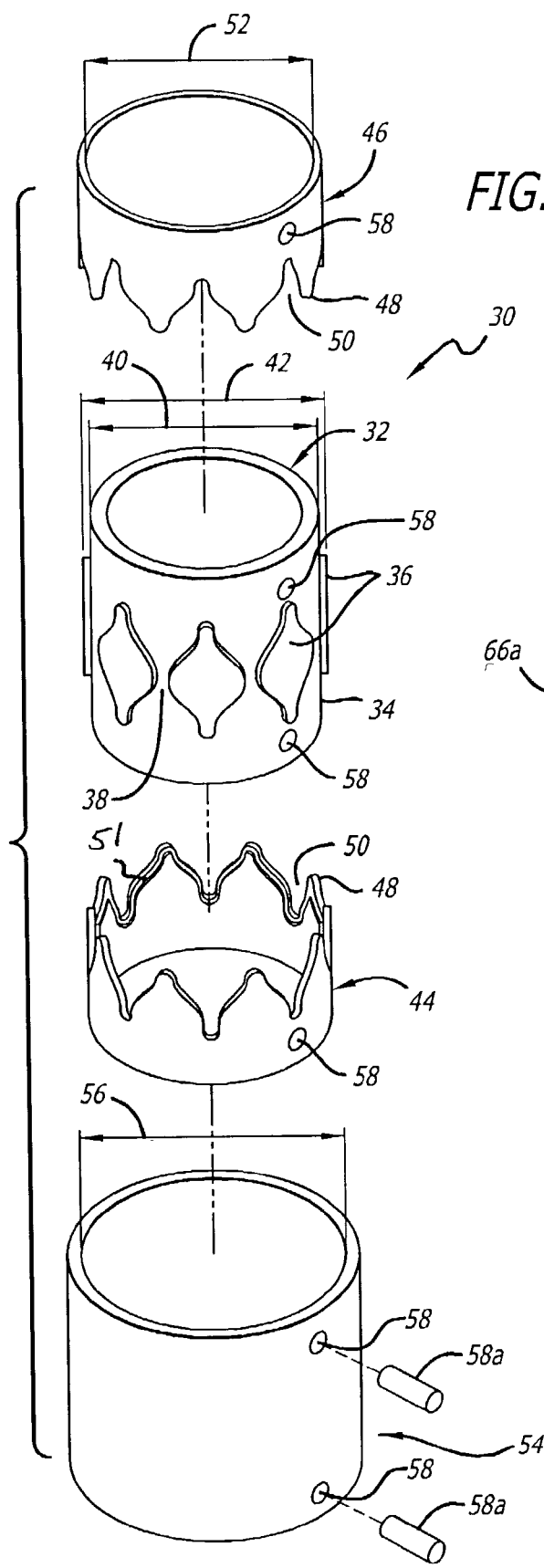
FIG. 6 is an exploded perspective view of one embodiment of the present invention.

In one embodiment, as shown in FIG. 6, a mandrel generally designated 30, for heating and setting elements of the stent 8, includes a central core cylinder 32 having an outer surface 34 with a plurality of raised forms 36, gaps 38 in-between the raised forms, and the central core cylinder also has an outer surface diameter 40 and a raised form diameter 42. The raised forms 36 may be in any shape which is desired for the stent cell 22, and in this embodiment the raised forms are almond-shape. The mandrel 30 also has a first outer cylinder 44 and a second outer cylinder 46, each having a curved radial end 48 with a cut-out design 50 similar to one-half the shape of the plurality of raised forms 36. In this embodiment, the cut-out designs 50 are one-half almond. The first and second outer cylinders 44 and 46 each have an inner diameter 52, the inner diameter is nearly equivalent to or slightly larger than the outer surface diameter 40 of the central core cylinder 32, and the inner diameter is lesser than the raised form diameter 42. The first and second outer cylinders 44 and 46 can be positioned on the central core cylinder 32 such that the curved radial ends 48 of the first and second outer cylinders align with the plurality of raised forms 36. In one embodiment, a ridge 51 is disposed on the inside surface of the first and second outer cylinders 44 and 46 following the edge of the cut-out design 50. The ridge 51 provides a gap having a width that is nearly equivalent to a thickness of a strut of a stent. In use, the ridge 51 will hold the strut against the central core cylinder 32.

The embodiment shown in FIG. 6, further includes a capture sleeve 54 having a cylindrical shape with an inner diameter 56 nearly equivalent to the raised form diameter 42 of the central core cylinder 32. The capture sleeve 54 slides over the central core cylinder 32 and the plurality of raised forms 36, leaving an insert space (not shown) for the first and second outer cylinders 44 and 46 to be inserted between the capture sleeve and the central core cylinder. In use, the capture sleeve 54 makes the shape-setting process easier by ensuring that the stent stays on the mandrel.

In one embodiment, the central core cylinder 62, first and second outer cylinders 44 and 46, and the capture sleeve 54 are all made of a heat conducting material such as aluminum or stainless steel, and all have at least one hole 58 disposed thereon. There may also be a plurality of holes 58 disposed on each piece 32, 44, 46, and 54 of the mandrel 30. The holes 58 may be used to orient and secure the cylinders through the use of one or more radial pins 58a. The holes 58 may also permit improved operation if the stent is heated by immersion in hot liquid such as a molten salt.

A method for forming a stent using the embodiment shown in FIG. 6 includes placing the stent on the central core cylinder 32, and directing the limb elements of the stent around the raised forms 36, so that the limb elements rest in the gaps 38 in-between the raised forms. Next, the capture sleeve 54 is placed over the central core cylinder 32 and stent, to retain the stent on the mandrel. The first and second outer cylinders 44 and 46 may then be inserted between the central core cylinder 32 and the capture sleeve 54 from opposite ends, such that the curved radial ends 48 force the stent into the shape of the raised forms 36 on the central core cylinder. The cylinders and sleeves may be secured by the insertion of radial pins 58a through the holes 58. After this step, heat is then applied to the mandrel 30 and stent to set the shape. In another embodiment, the capture sleeve 54 may not be used, so that after the stent is placed on the central core cylinder 32 around the plurality of raised forms 36, the first and second outer cylinders 44 and 46 are then placed on opposite ends of the mandrel such that the curved radial ends 48 force the stent into the shape of the raised forms. This shape setting method can be applied to any nitinol stent.

Figure 7:
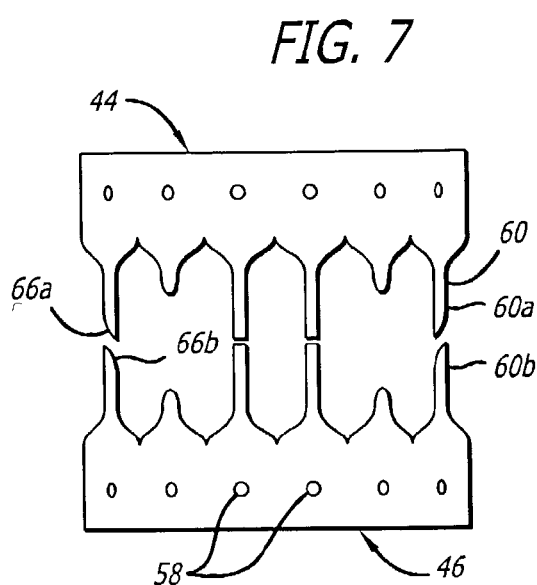
FIG. 7 is an elevational view of the first and second outer cylinders having hook extenders.
Figure 8:
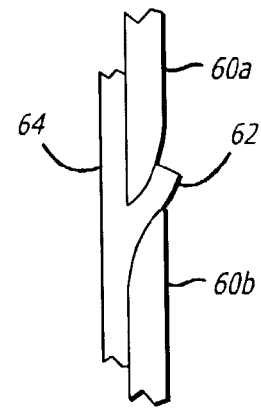
FIG. 8 is a partial elevational view of hook extenders shaping a hook of a stent.

In another embodiment of the apparatus as shown in FIG. 7, the first and second outer cylinders 44 and 46 have a plurality of hook extenders 60 disposed at the curved radial ends 48, in order to shape set hooks 62 found on a stent 64. This embodiment is for the expansion of a nitinol stent on the last stage of expansion. FIG. 8 shows a partial view of a top hook extender 60a on the first or top outer cylinder 44, and a bottom hook extender 60b on the second or bottom outer cylinder 46, shaping a hook 62 located in-between the two hook extenders. The top and bottom hook extender 60a and 60b each have a curved tip 66a and 66b respectively, and the curved tip 66a faces curved tip 66b, so that when the first and second outer cylinders 44 and 46 are in position on the central core cylinder 32, the curved tips 66a and 66b are complementary to each other. In this embodiment, the top and bottom outer cylinders 44 and 46 are used in conjunction with the central core cylinder 32, but not the capture sleeve 54. The first and second outer cylinders 44 and 46 are made of a heat conducting material such as aluminum, but it is preferred to use 300 series stainless steel. All or some of the cylinders and sleeves may be coated or plated with substances such as titanium nitride to improve operation or extend the service life of the cylinders and sleeves.

A method of forming a stent using this embodiment, includes placing the stent 64 on the central core cylinder 32 and directing limb elements 68 of the stent around the raised forms 36. Next, the first and second outer cylinders 44 and 46 are placed on opposite ends of the central core cylinder 32 such that the curved radial ends 48 force the stent into the shape of the raised forms 36, and the hook extenders 60 shape the hooks 62 of the stent 64. Once the cylinders 44 and 46 are in place, heat is then applied to set the shape of the stent. This method makes the shape-setting process easier, and helps achieve uniformity of stent cells and hooks after expansion.

Figure 9:
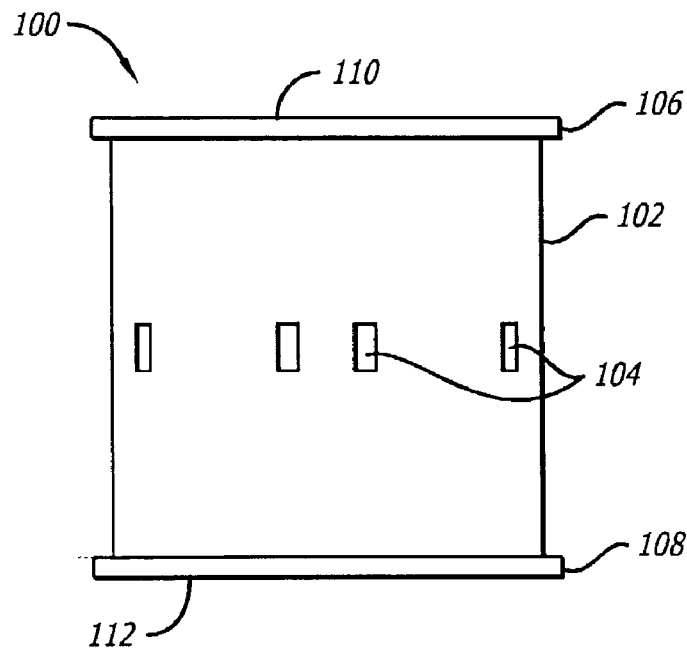
FIG. 9 is an elevational view of another embodiment of the present invention.
Figure 10:
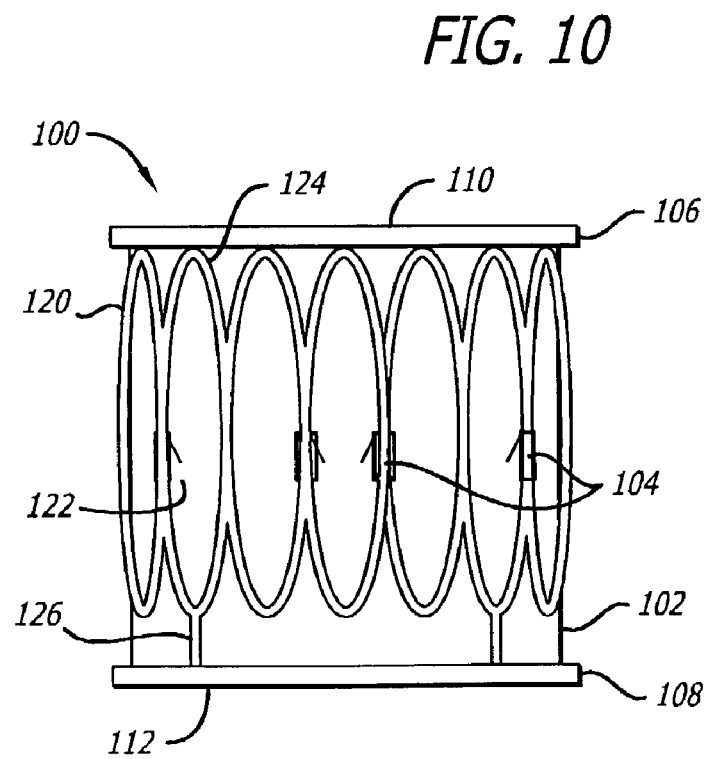
FIG. 10 is an elevational view of the embodiment shown in FIG. 4 with a stent in position on the mandrel.
Figure 11:
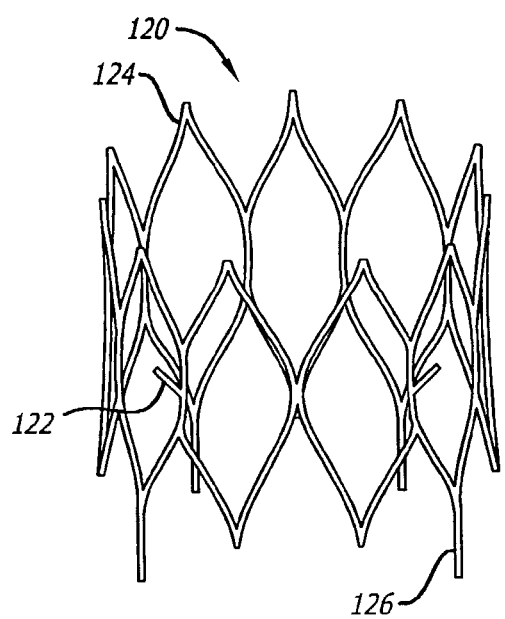
FIG. 11 is a perspective view of a stent with the hooks facing outward.
Figure 13:
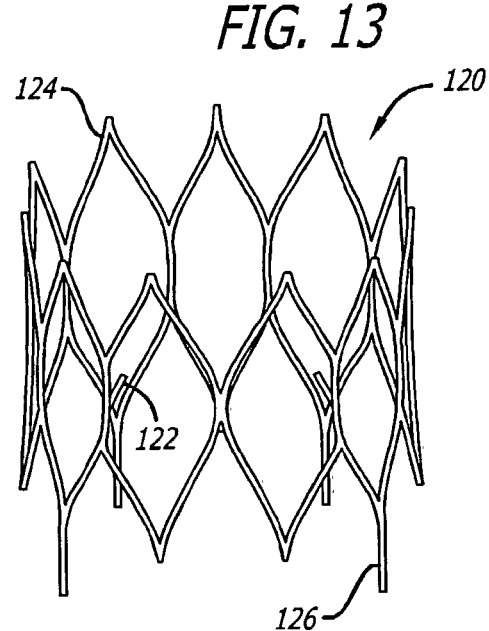
FIG. 13 is a perspective view of a stent turned inside-out with the hooks facing inward.
Figure 12:
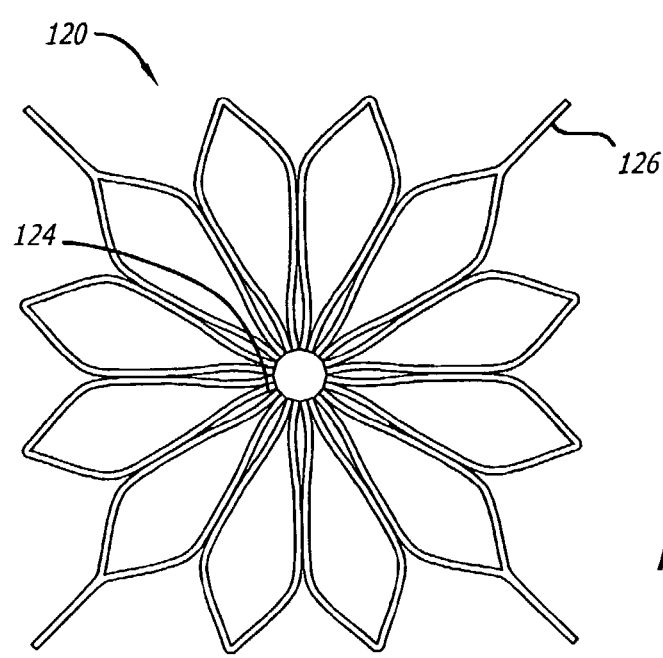
FIG. 12 is a perspective view of a stent pushed flat against a surface.

Now referring to FIGS. 9 and 10, another embodiment is shown of a mandrel 100 used for heating and setting hooks 122 of a stent 120 (shown in FIGS. 11, 12 and 13). The mandrel 100 has an outer surface 102 with a plurality of slots 104 disposed thereon corresponding to the position of hooks 122 on the stent 120. The mandrel 100 may also include first and second stop rings 106 and 108 constructed to engage a top end 110 and a bottom end 112 of the mandrel 100, and to press against a top end 124 and a bottom end 126 of the stent 120, so that the first and second stop rings keep the stent from moving and hold the hooks inside the plurality of slots 104. In this embodiment, there are no additional rings placed over the stent to shape the hooks or barbs, and therefore the stent is less prone to damage.

A method for setting the hooks 122 of a stent 120 using the mandrel 100 with a plurality of slots 104, includes turning the stent inside-out. As shown in FIG. 11, the stent 120 has the hooks 122 pointed toward the outside, and once the stent is turned inside-out, the hooks are pointed toward the inside of the stent as shown in FIG. 13. The stent 120 may be turned inside-out manually by pressing the top end 124 downward so the stent becomes flattened with the top end forming an inner diameter, and the bottom end 126 forming an outer diameter as shown in FIG. 12. From this position, the top end 124 is held down, while the bottom end 126 is pulled upward, so that the hooks 122 face inward as shown in FIG. 13. After the stent 120 is turned inside-out, the stent is positioned on the mandrel 100 such that the hooks 122 are aligned with the plurality of slots 104. The hooks 122 are then pushed into the slots 104, and heat is applied to set the hooks.

This method may further include engaging the first and second stop rings 106 and 108 at the top and bottom ends 110 and 112 of the mandrel respectively, such that the first and second stop rings press against the top and bottom ends 124 and 126 of the stent, thereby holding the stent in place during heating. This method makes the hook-setting step much easier, faster, and the stent is less likely to be damaged. This method can apply to any super elastic stent (at or below 37° C.) with hooks or barbs, which require thermal shape setting.

Heating and setting procedures vary for particular stent designs and stent materials but are in general, conventionally known in the art.

While several particular forms of the invention have been illustrated and described, it will also be apparent that various modifications can be made without departing from the spirit and scope of the invention. Accordingly, it is not intended that the invention be limited, except as by the appended claims.

We claim:

1. An apparatus for heating and setting elements of a stent, comprising:
   a central core cylinder having an outer surface including a plurality of raised forms, each raised form having a shape similar to a stent cell shape, and the central core cylinder having an outer surface diameter and a raised form diameter; and
   a sleeve including an inclined surface to facilitate formation of a hook.

2. The apparatus of claim 1, further comprising a capture sleeve having a cylindrical shape with an inner diameter nearly equivalent to the raised form diameter of the central core cylinder, the capture sleeve fitting over the central core cylinder and the plurality of raised forms to hold a stent in position on the central core cylinder.

3. The apparatus of claim 1, further comprising a first and second outer cylinder, each having a curved radial end with a cut-out design similar to one-half the shape of the plurality of raised forms, and the first and second outer cylinders each having an inner diameter, the inner diameter being nearly equivalent to the outer surface diameter of the central core cylinder, whereby the first and second outer cylinders are positioned on the central core cylinder such that the curved radial ends of the first and second outer cylinders align with the plurality of raised forms.

4. The apparatus of claim 3, wherein the first and second outer cylinders have a plurality of hook extenders disposed at the curved radial ends.

5. The apparatus of claim 3, further comprising a capture sleeve having a cylindrical shape with an inner diameter nearly equivalent to the raised form diameter of the central core cylinder, the capture sleeve fitting over the central core cylinder and the plurality of raised forms, leaving an insert space for the first and second outer cylinders to be inserted between the capture sleeve and the central core cylinder.

6. The apparatus of claim 1, wherein each raised form has an almond shape.

7. An apparatus for heating and setting elements of a stent, comprising:
   a central core cylinder having an outer surface including a plurality of raised forms, each raised form having an almond shape, and the central core cylinder having an outer surface diameter and a raised form diameter; and
   a first and second outer cylinder, each having a curved radial end with a cut-out design having a plurality of one-half almond shapes, and the first and second outer cylinders each having an inner diameter, the inner diameter being nearly equivalent to the outer surface diameter of the central core cylinder, whereby the first and second outer cylinders are positioned on the central core cylinder such that the curved radial ends of the first and second outer cylinders align with the plurality of raised forms.

8. The apparatus of claim 7, further comprising a capture sleeve having a cylindrical shape with an inner diameter nearly equivalent to the raised form diameter of the central core cylinder, the capture sleeve fitting over the central core cylinder and the plurality of raised forms, leaving an insert space for the first and second outer cylinders to be inserted between the capture sleeve and the central core cylinder.

9. The apparatus of claim 7, wherein the first and second outer cylinders each include a plurality of hook extenders disposed at the curved radial end.

* * * * *